(12) United States Patent
Kim et al.

(10) Patent No.: US 9,206,287 B2
(45) Date of Patent: Dec. 8, 2015

(54) FLUORENE DERIVATIVES AND LENS USING THE SAME

(71) Applicant: Samsung Electro-Mechanics Co., Ltd., Suwon-si (KR)

(72) Inventors: Jun Young Kim, Suwon-Si (KR); Ichiro Ogura, Suwon-Si (KR); Ick Chan Shim, Suwon-Si (KR)

(73) Assignee: Samsung Electro-Mechanics Co., Ltd., Suwon-si (KR)

( * ) Notice: Subject to any disclaimer, the term of this patent is extended or adjusted under 35 U.S.C. 154(b) by 0 days.

(21) Appl. No.: 14/449,927

(22) Filed: Aug. 1, 2014

(65) Prior Publication Data

US 2015/0025215 A1 Jan. 22, 2015

Related U.S. Application Data

(63) Continuation of application No. 14/288,368, filed on May 27, 2014, now abandoned.

(30) Foreign Application Priority Data

| May 28, 2013 | (KR) | 10-2013-0060651 |
| May 13, 2014 | (KR) | 10-2014-0057361 |

(51) Int. Cl.

| *C08G 63/02* | (2006.01) |
| *C08G 64/24* | (2006.01) |
| *C07C 43/23* | (2006.01) |
| *G02B 1/04* | (2006.01) |
| *C08G 63/187* | (2006.01) |

(52) U.S. Cl.
CPC ............... *C08G 64/24* (2013.01); *C07C 43/23* (2013.01); *C08G 63/187* (2013.01); *G02B 1/041* (2013.01); *C07C 2103/18* (2013.01)

(58) Field of Classification Search
CPC ...................................................... C08G 63/605
USPC .................................. 528/190, 192, 193, 194
See application file for complete search history.

(56) References Cited

U.S. PATENT DOCUMENTS

| 5,391,650 | A | * | 2/1995 | Brennan et al. ............... 525/523 |
| 8,026,336 | B2 | * | 9/2011 | Kato et al. .................... 528/196 |

FOREIGN PATENT DOCUMENTS

| EP | 2757395 | | 7/2014 |
| JP | 2001-106761 A | | 4/2001 |
| JP | 2007057916 | * | 3/2007 |
| WO | 2013/039178 | | 3/2013 |

OTHER PUBLICATIONS

Jin Won Kim et al. 2286 Bull. Korean Chem. Soc. 2013, vol. 34, No. 8 Efficient Ring Opening Reaction of Epoxides with Oxygen Nucleophiles Catalyzed by Quaternary Onium Satin; Department of Chemistry, Yeungnam University, Gyeongsan, Gyeongbuk 712-749, Korea.Received Apr. 5, 2013, Accepted May 5, 2013.*
Office action dated Oct. 14, 2014 from corresponding European Patent Application No. 14169749.0.

* cited by examiner

*Primary Examiner* — Terressa Boykin
(74) *Attorney, Agent, or Firm* — NSIP Law

(57) ABSTRACT

Fluorene derivatives are described including those having optical properties which can make them suitable for use in optical systems such as cameras. Various derivatives can have high polarity, small molecular volume, low glass transition temperature, high transparency and/or excellent optical characteristics. In addition, a process for making the fluorene derivatives and products made from the fluorene derivatives are described.

16 Claims, 5 Drawing Sheets

FLUORENE DERIVATIVES AND LENS USING THE SAME

CROSS REFERENCE TO RELATED APPLICATION

This application is a continuation of U.S. patent application Ser. No. 14/288,368, filed on May 27, 2014, entitled "Fluorene derivatives and lens using the same," which claims priority to Korean Patent Application No. 10-2013-0060651, filed on May 28, 2013, entitled "Fluorene Derivatives and Lens Using the Same", to and Korean Patent Application No. 10-2014-0057361, filed on May 13, 2014, entitled "Fluorene Derivatives and Lens Using the Same", all of which are hereby incorporated by reference in their entireties into this application.

BACKGROUND OF THE INVENTION

1. Technical Field

Embodiments of the present invention relate to fluorene derivatives and relate to lenses using the same.

2. Background

Optical glass and transparent optical resin can be used as a material for an optical element in optical systems of various kinds including cameras, such as cameras for smart phones, video cameras, and the like.

Various kinds of materials can be used for optical glass, such as those having favorable heat resistance, transparency, dimensional stability, and chemical resistance, and the like. Materials can have various refractive indexes (nD) or abbe numbers (uD), but some materials can be expensive and can have low formability and low productivity. In some cases, such as some cases where the glass is used for an aspheric lens used in aberration correction, a significantly high technology cost and a high material cost can limit the use of the optical glass.

In some embodiments, an optical lens can be made of an optically transparent resin. In some embodiments, a thermoplastic transparent resin can have advantages in that an optical lens may be mass-produced by injection molding and easily processed into the aspheric lens, such that the optical lens can be used as a lens for a camera. In some cases, a resin composition containing a polycondensation polymer or polyaddition polymer having a fluorene compound as a monomeric unit and at least one sulfur atom in a repeating unit can be used and formed into an optical element by injection molding the resin composition.

SUMMARY OF THE INVENTION

Embodiments of the present disclosure have been made in an effort to provide a fluorene derivative having a high polarity and a small molecular volume with excellent optical characteristics exhibited.

In addition, embodiments of the present disclosure have been made in an effort to provide a fluorene derivative having a low glass transition temperature (Tg) with work facility and forming facility.

Further, embodiments of the present disclosure have been made in an effort to provide a fluorene derivative having high transparency.

In addition, embodiments of the present disclosure have been made in an effort to provide an eco-friendly fluorene derivative.

Further, embodiments of the present disclosure have been made in an effort to provide a copolymer of the fluorene derivative.

Furthermore, embodiments of the present invention have been made in an effort to provide a lens comprising a copolymer of the fluorene derivative.

Furthermore, embodiments of the present invention have been made in an effort to provide a lens made by forming a copolymer of the fluorene derivative.

According to an embodiment of the present disclosure, there is provided a fluorene derivative represented by the following Chemical Formula 1:

[Chemical Formula 1]

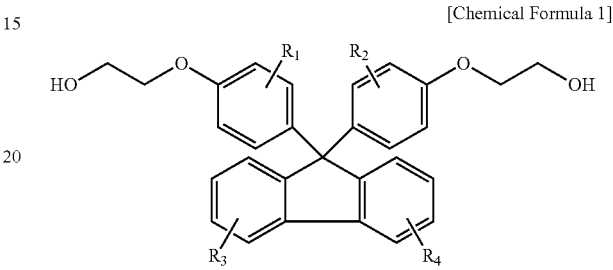

wherein $R_1$, $R_2$, $R_3$, and $R_4$ are the same as or different from each other, and are H or represented by the following Chemical Formula 2, and at least two of $R_1$, $R_2$, $R_3$, and $R_4$ are independently selected from compounds represented by the following Chemical Formula 2:

$$—R_5—Ar \qquad \text{[Chemical Formula 2]}$$

in Chemical Formula 2, $R_5$ is a (C1-C5) alkanediyl group, and Ar is a (C6-C22) aryl group. (The subscripts provided on the R groups identify different R groups, rather than indicating the number of R groups present.)

According to another embodiment of the present disclosure, there is provided a copolymer of a compound represented by Chemical Formula 1.

According to another embodiment of the present disclosure, there is provided a lens manufactured by molding a copolymer of a compound represented by Chemical Formula 1.

According to another embodiment of the present disclosure, there is provided a lens comprising a copolymer of a compound represented by Chemical Formula 1.

According to another embodiment of the present disclosure, there is provided a copolymer of Formula 3, Formula 4, Formula 5 or Formula 6 as shown below:

(Chemical Formula 3)

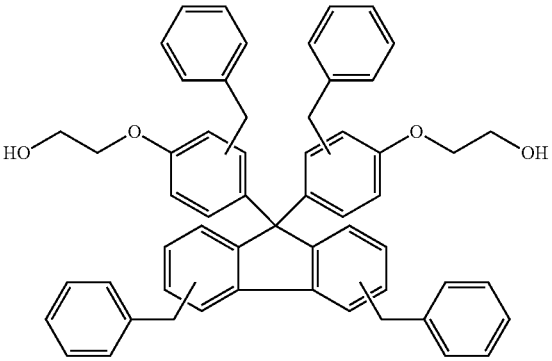

(Chemical Formula 4)

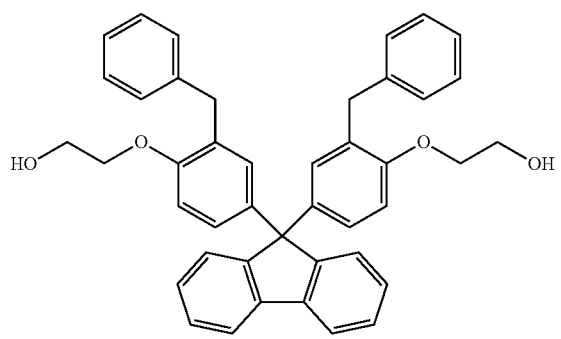

(Chemical Formula 5)

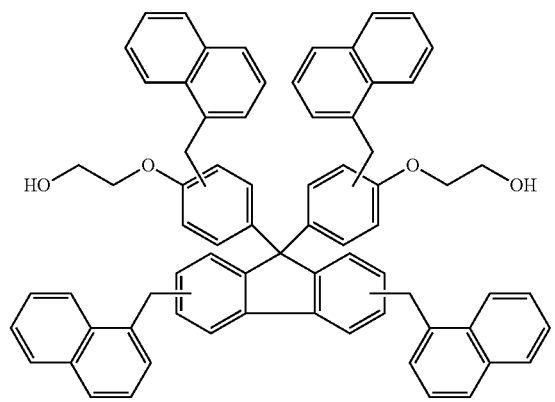

(Chemical Formula 6)

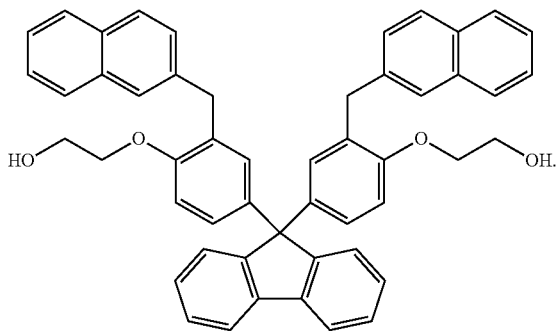

and of a dicarboxylic acid or phosgene.

BRIEF DESCRIPTION OF THE DRAWINGS

The above and other objects, features and advantages of the present invention will be more clearly understood from the following detailed description taken in conjunction with the accompanying drawings, in which.

DESCRIPTION OF THE EMBODIMENTS

Figure 1:
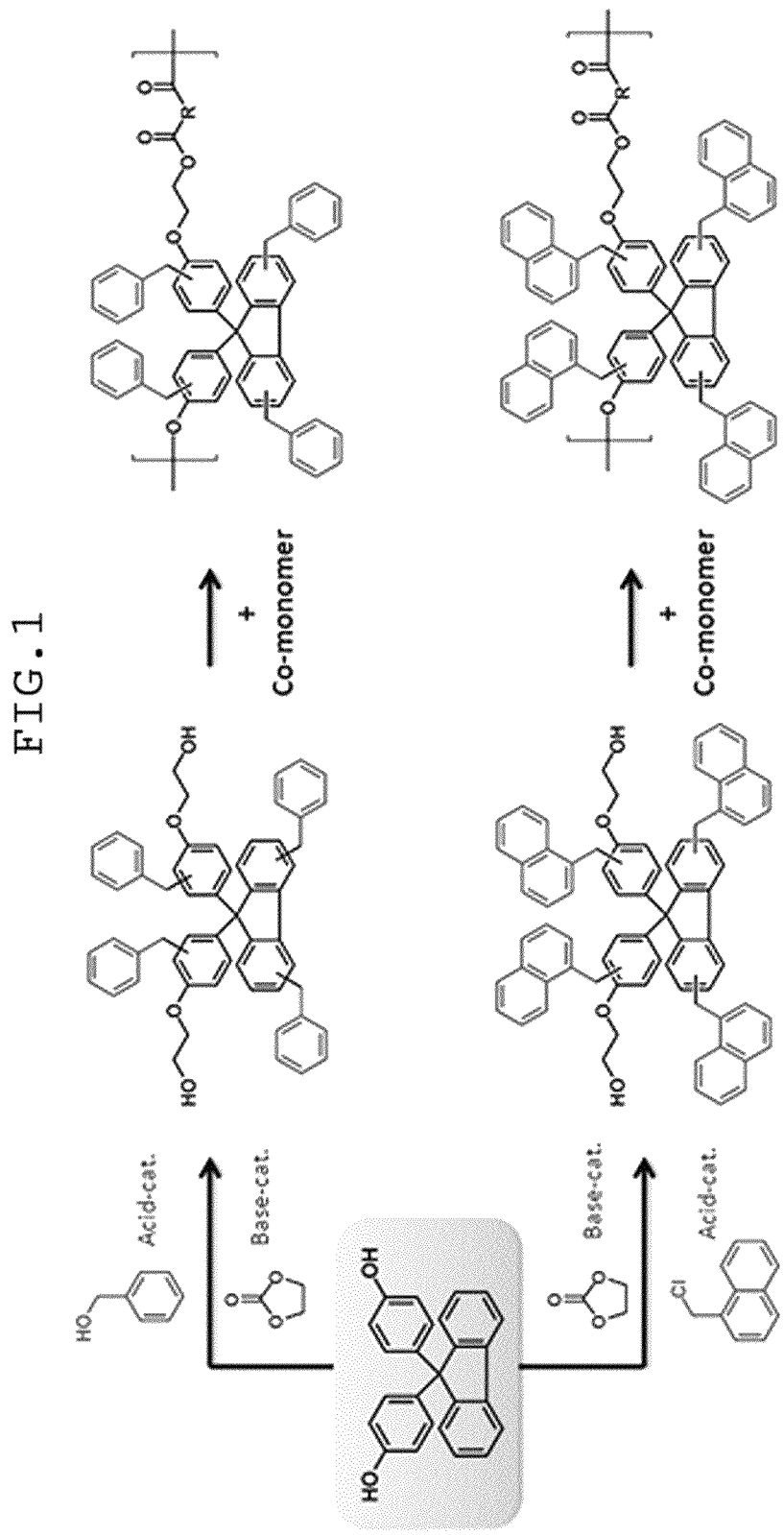
FIG. 1 is a view showing a schematic synthesis scheme of a copolymer of a fluorene derivative according to an embodiment of the present disclosure.

The aspects, features and advantages of the present disclosure will be more clearly understood from the following detailed description of the embodiments taken in conjunction with the accompanying drawings. Throughout the accompanying drawings, the same reference numerals are used to designate the same or similar components, and redundant descriptions thereof are omitted. Further, in the following description, the terms "first", "second", "one side", "the other side" and the like are used to differentiate a certain component from other components, but the configuration of such components should not be construed to be limited by the terms. Further, in the description of the present invention, when it is determined that the detailed description of the related art would obscure the gist of the present invention, the description thereof will be omitted.

Hereinafter, embodiments of the present disclosure will be described in detail with reference to the attached drawings.

Fluorene Derivatives

The fluorene derivatives according to an embodiment of the present invention can be represented by the following Chemical Formula 1:

Chemical Formula 1

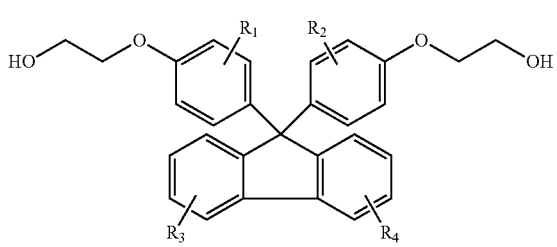

In Chemical Formula 1, $R_1$, $R_2$, $R_3$, and $R_4$ are the same as or different from each other and are H or represented by the following Chemical Formula 2, and at least two of $R_1$, $R_2$, $R_3$, and $R_4$ are independently selected from compounds represented by the following Chemical Formula 2:

—$R_5$—Ar  Chemical Formula 2

In Chemical Formula 2, $R_5$ is a (C1-C5) alkanediyl group, and Ar is a (C6-C22)aryl group.

In some embodiments of the fluorene derivative, an aryl group having a small molecular volume can be provided in at least two of the $R_1$-$R_4$ groups which can be attached to at least two of the benzene moieties in a fluorene structural unit.

In some embodiments of the fluorene derivative, an aryl group having a small molecular volume can be provided in at least two of the R₁-R₄ groups which can be attached to at least two of the benzene moieties in a fluorene structural unit, such that a polarity of the fluorene derivative itself may be increased and/or the refractive index can be improved.

In some embodiments, an alkanediyl group of the R-group, can have a rotatable bond in the $R_5$ group which can be attached to an aromatic ring of Formula 1.

In some embodiments, an alkanediyl group of the R-group, can have a rotatable bond in the $R_5$ group which can be attached to an aromatic ring of Formula 1, such that Tg can be decreased and/or a viscosity may be decreased and/or formability may be improved and/or workability may be improved.

In various embodiments, the fluorene derivative is made without a halogen substituent, such as Br or Cl, which can result in a more eco-friendly product and process and reduced or eliminated potential for dioxin side product or contaminants. In various embodiments, a sulfur or nitrogen atom is not used. In some embodiments, a sulfur or nitrogen atom is not used which can result in greater transparency.

Here, according to an embodiment, Ar may be a phenyl group.

According to another embodiment, Ar may be a naphthyl group.

According to still another embodiment, Ar may be a biphenyl group.

According to still another embodiment, Ar may be an anthryl group.

According to still another embodiment, Ar may be a phenanthryl group.

The fluorene derivative represented by Chemical Formula 1 may be a compound represented by the following Chemical Formula 3.

The fluorene derivative represented by Chemical Formula 1 may be a compound represented by the following Chemical Formula 4.

[Chemical Formula 4]

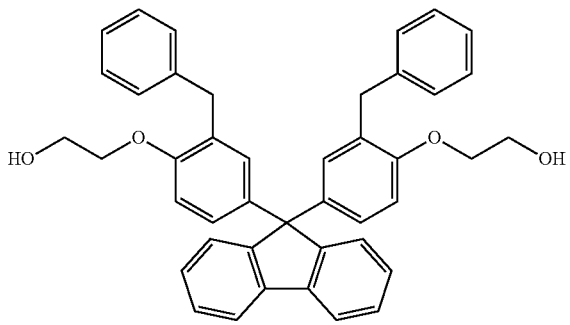

More specifically, in the compound represented by Chemical Formula 4, a benzyl group is introduced to two benzene moieties in the fluorene structural unit of Formula 1, such that a polarity of the fluorene derivative itself may be improved, and improving the refractive index. Further, the methylene group of each benzyl group is attached to a benzene moiety of the fluorene structural unit of Formula 1, as shown in Formula 4 such that the benzyl group itself may rotate and a viscosity of the derivative may be decreased, and formability and workability may be improved.

The fluorene derivative represented by Chemical Formula 1 may be a compound represented by the following Chemical Formula 5.

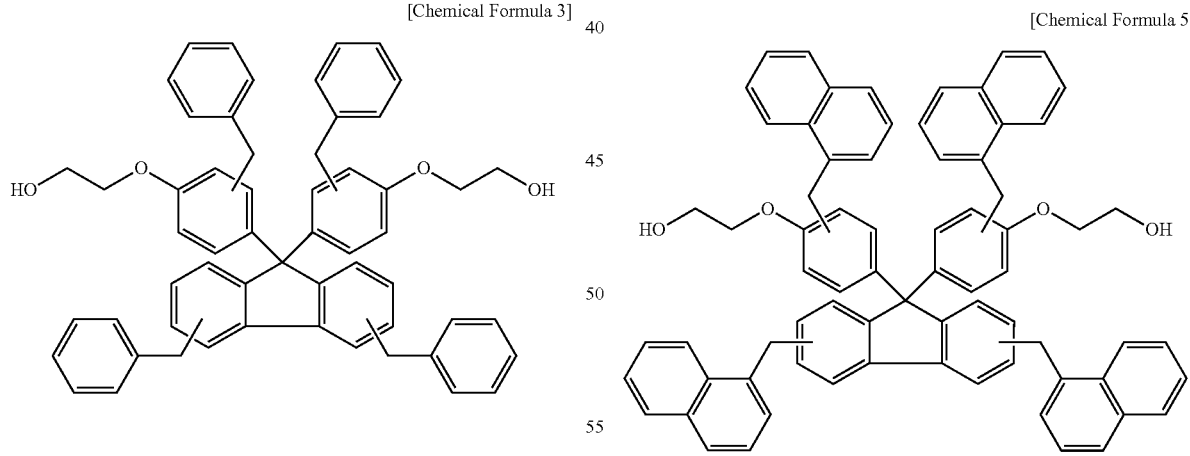

[Chemical Formula 3]

[Chemical Formula 5]

More specifically, in the compound represented by Chemical Formula 3, a benzyl group is introduced to the four benzene moieties in the fluorene structural unit of Formula 1, such that a polarity of the fluorene derivative itself may be improved, and improving the refractive index. Further, the methylene group of each benzyl group is attached to the benzene moiety of the fluorene structural unit of Formula 1, as shown in Formula 3, such that the benzyl group itself may rotate, and a viscosity of the derivative may be decreased, and formability and workability may be improved.

More specifically, in the compound represented by Chemical Formula 5, a methyl naphthyl group is introduced to the four benzene moieties in the fluorene structural unit of Formula 1, such that a polarity of the fluorene derivative itself may be improved, and improving the refractive index. Further, the methylene group of each naphthyl group is attached to the benzene moiety of the fluorene structural unit of Formula 1, as shown in Formula 5 such that the methyl naphthyl group itself may rotate and a viscosity of the derivative may be decreased, and formability and workability may be improved.

The fluorene derivative represented by Chemical Formula 1 may be a compound represented by the following Chemical Formula 6.

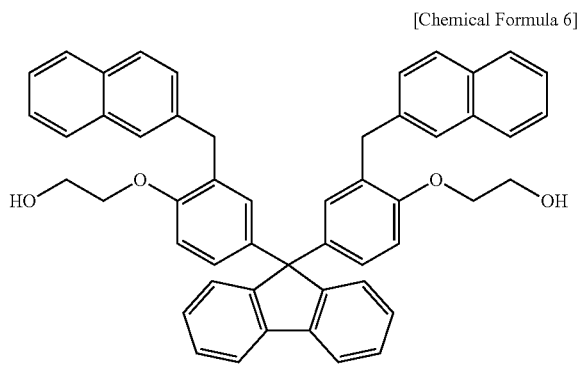 [SMILES: OCCOc1ccc(C2(c3ccc(OCCO)c(Cc4ccc5ccccc5c4)c3)c3ccccc3-c3ccccc32)cc1Cc1ccc2ccccc2c1]

[Chemical Formula 6]

More specifically, in the compound represented by Chemical Formula 6, a methyl naphthyl group is introduced to two benzene moieties in the fluorene structural unit of Formula 1, such that a polarity of the fluorene derivative itself may be improved, and improving the refractive index. Further, the methylene group of each methyl naphthyl group is attached to the benzene moiety of the fluorene structural unit of Formula 1, as shown in Formula 6 such that the methyl naphthyl group itself may rotate, and a viscosity of the derivative may be decreased, and formability and workability may be improved.

Preparation Method of Fluorene Derivative

Hereinafter, a preparation method of a fluorene derivative according to an embodiment of the present invention will be described in detail. However, the specific Reaction Formula described below is to illustratively explain the preparation method, and it may be appreciated by those skilled in the art that the preparation method of a fluorene derivative is not particularly limited thereto.

In one embodiment, a compound represented by Chemical Formula 3 may be synthesized by carrying out a B-alkyl Suzuki coupling reaction using a 2,7-dibromo-9-fluorene using a starting compound and then carrying out a fluorene structure building reaction as shown in the following Reaction Formula 1.

[Reaction Formula 1]

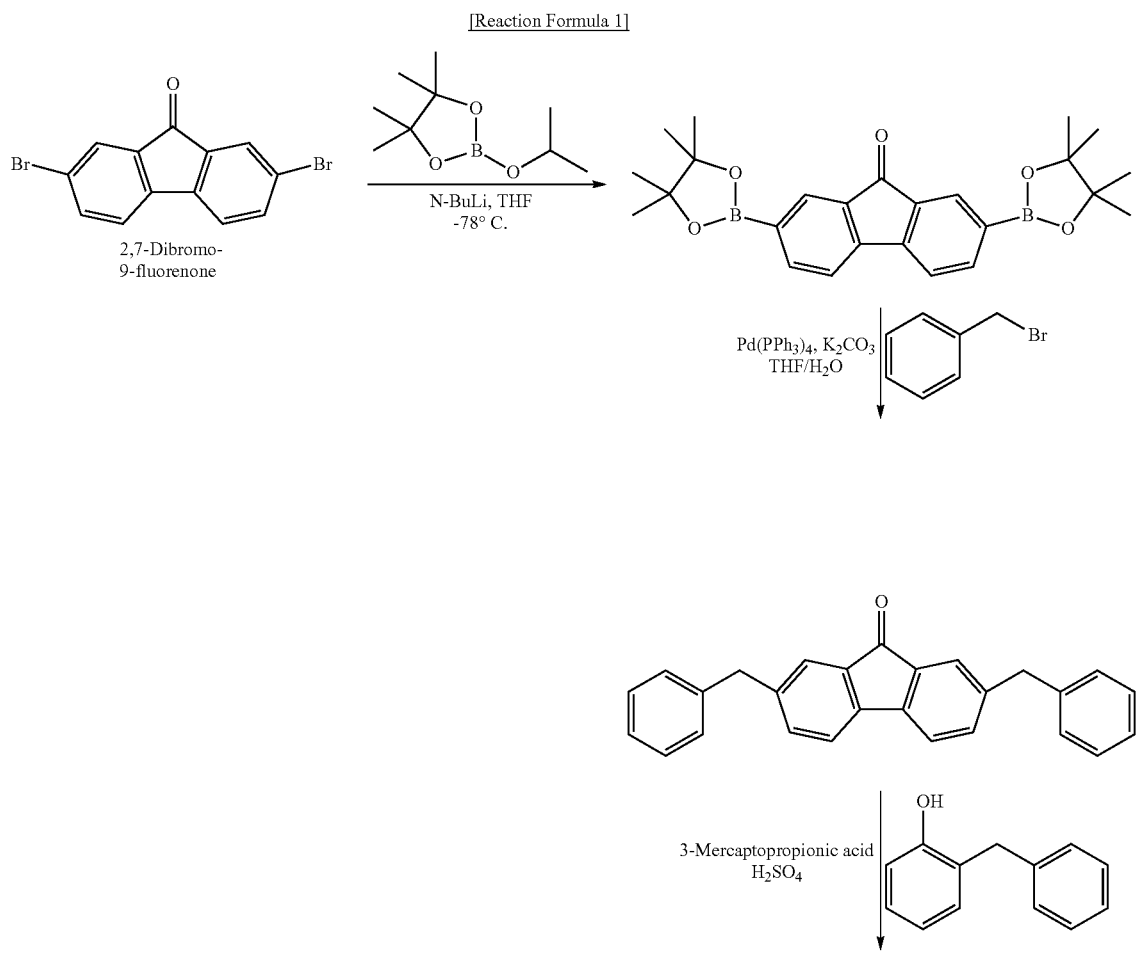

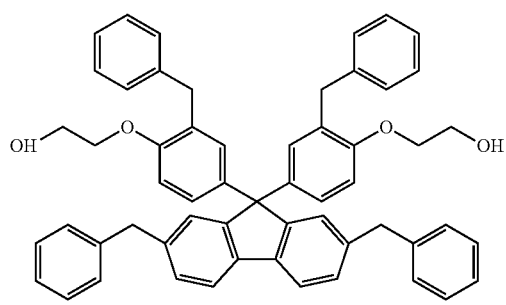
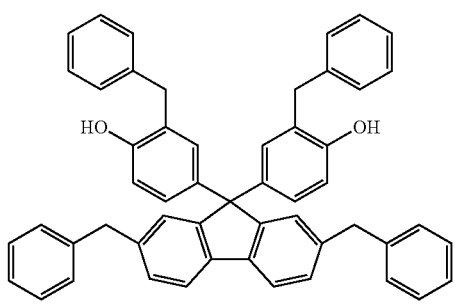

According to another embodiment, the compound represented by Chemical Formula 3 may be synthesized by a reaction represented by the following Reaction Formula 2.

[Reaction Formula 2]

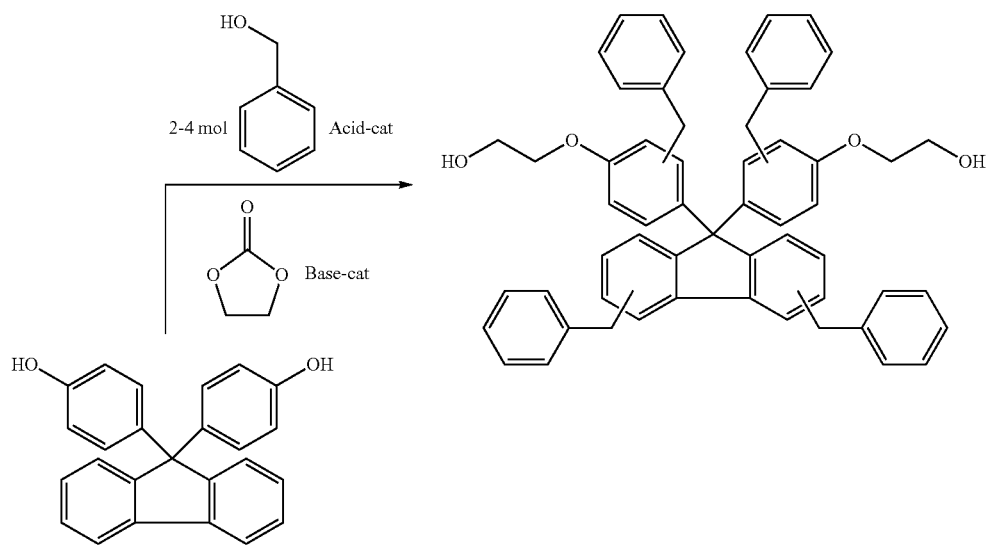

In various embodiments, a base catalyst may be used instead of an acid catalyst, and benzyl chloride may be used instead of benzyl alcohol to react with fluorene bisphenol.

In another embodiment, a compound represented by Chemical Formula 4 may be synthesized using a 9-fluorenone as a starting material as shown in the following Reaction Formula 3.

[Reaction Formula 3]

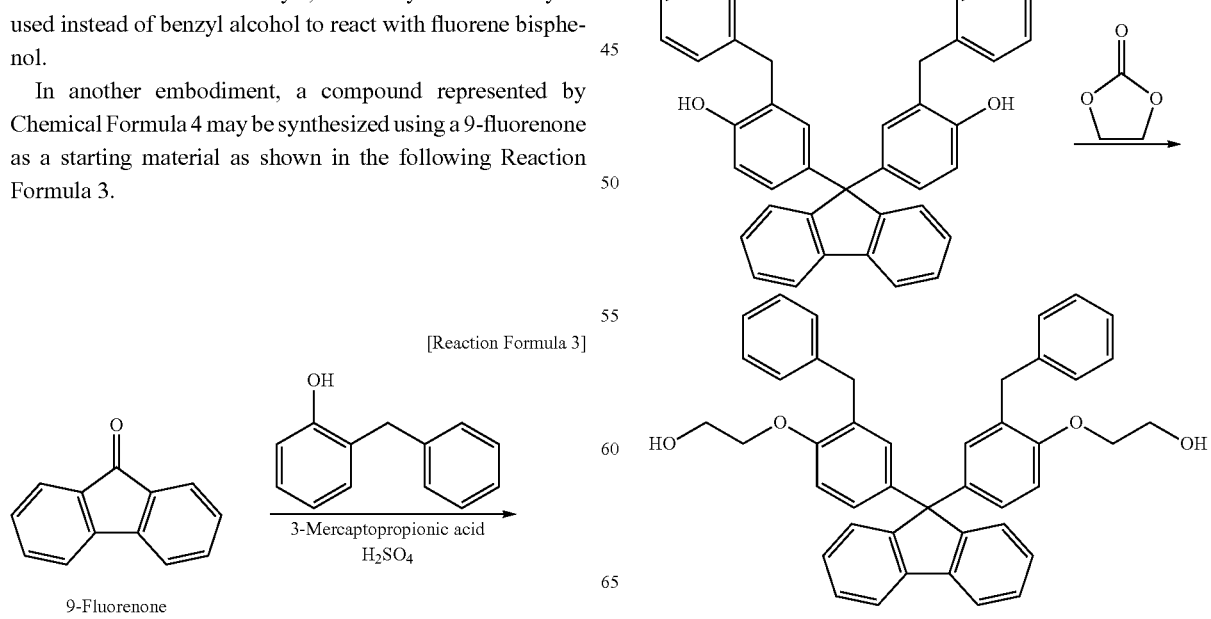

While o-benzyl phenol is shown in Reaction Formula 3, in additional embodiments m-benzyl phenol may be used depending on the desired position(s) of the substituent.

In another embodiment, a compound represented by Chemical Formula 5 may be synthesized by a reaction as shown in the following Reaction Formula 4 according to an embodiment.

Copolymer

A copolymer according to an embodiment of the present disclosure can be a copolymer of the fluorene derivative represented by Chemical Formula 1. Hereinafter, a specific example of the copolymer will be described, but the following compound is provided as an example for illustrative purpose,

[Reaction Formula 4]

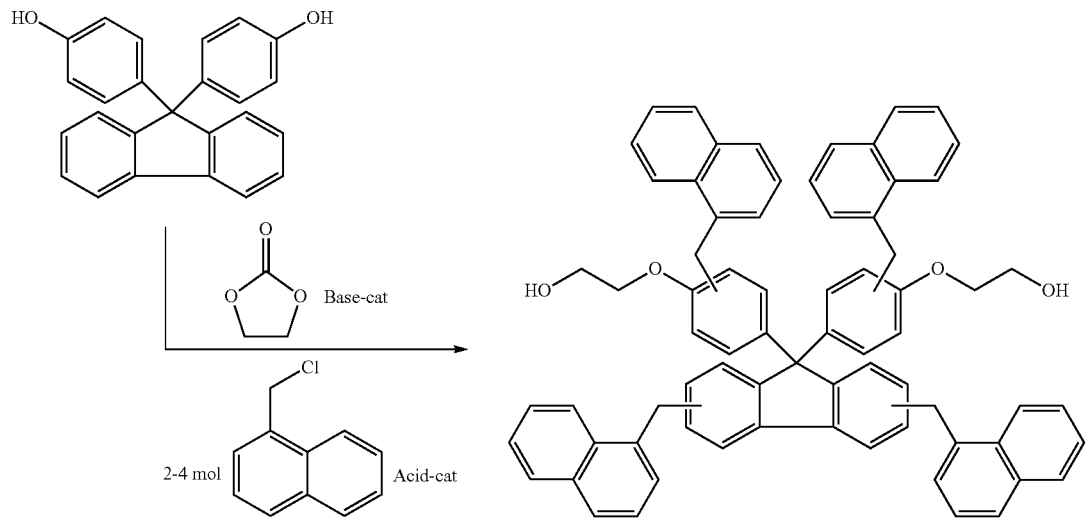

In additional embodiments, 1-naphthyl methanol may be used instead of 1-(chloromethyl)naphthalene reacting with fluorene bisphenol.

In another embodiment, a compound represented by Chemical Formula 6 may be synthesized using 9-fluorenone as a starting material as shown in the following Reaction Formula 5.

and the copolymer of the present invention is not particularly limited thereto.

For example, in the case of obtaining the copolymer by copolymerizing the fluorene derivative of Chemical Formula 3 in which the benzyl group is introduced to four benzene moieties in the fluorene structural unit of Formula 1, the

[Reaction Formula 5]

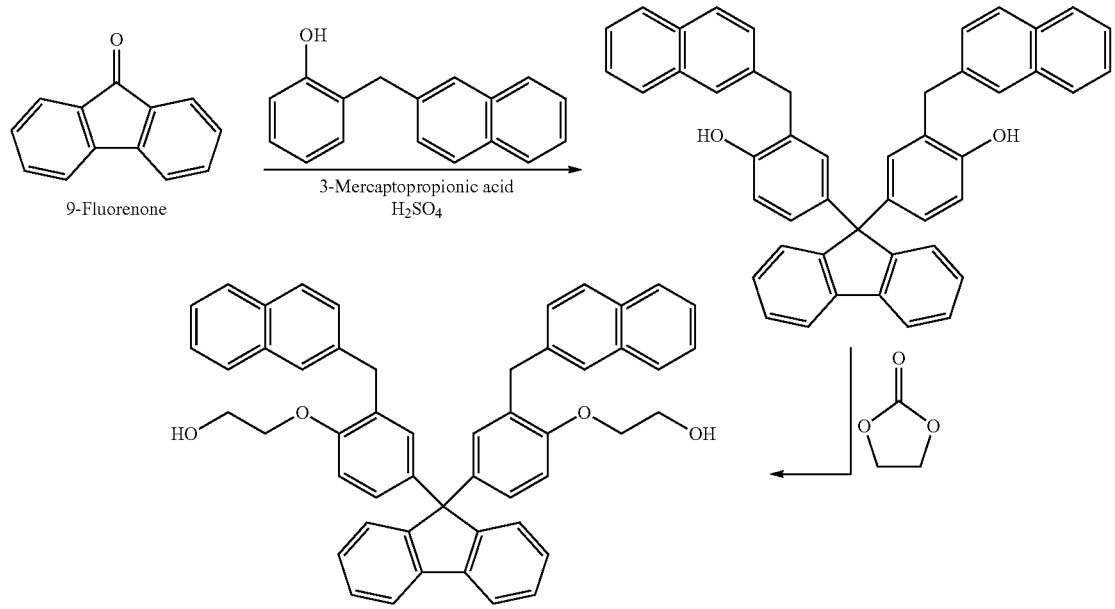

copolymer may be represented by the following Chemical Formula 7.

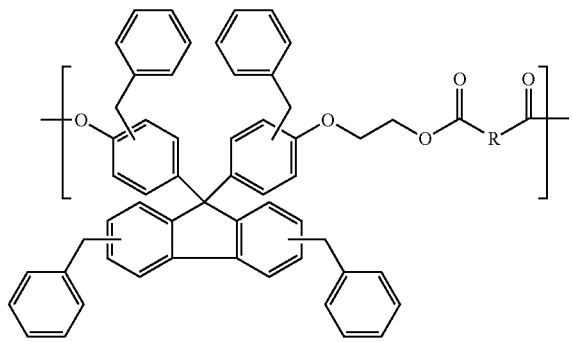

[Chemical Formula 7]

thalene dicarboxylic acid, anthracene dicarboxylic acid, and the like, and biphenyl dicarboxylic acid such as 2,2'-biphenyl dicarboxylic acid, and the like. In addition, acid anhydrides such as hexahydrophthalic acid anhydride, tetrahydrophthalic acid anhydride, and the like, lower (C1-C4)alkylester such as dimethylester, diethylester, and the like, a reactive derivative thereof such as a derivative capable of forming ester corresponding to dicarboxylic acid, for example, acid halide or the like, may be used. R may be changed according to a kind of monomer actually used at the time of copolymerization.

For example, in the case of obtaining the copolymer by copolymerizing the fluorene derivative of Chemical Formula 5 in which the methyl naphthyl group is introduced in four benzene moieties in the fluorene structural unit, the copolymer may be represented by the following Chemical Formula 8.

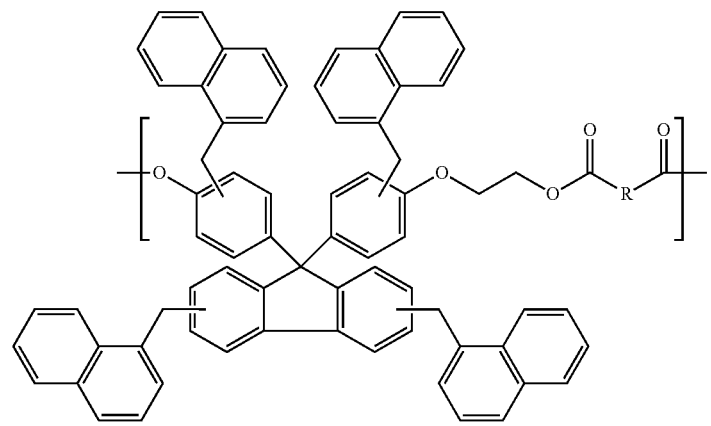

[Chemical Formula 8]

In Chemical Formula 7, R, which is a dicarboxylic acid component, may be a part of a dicarboxylic acid, a dicarboxylic acid derivative, a dicarboxylic acid derivative capable of forming an ester bond, an ester-forming dicarboxylic acid derivative, or the like. The dicarboxylic acid/derivative may be used alone or a combination of two or more dicarboxylic acids/derivatives may be used. A representative example of dicarboxylic acid may include aliphatic dicarboxylic acid, for example, alkane dicarboxylic acid such as oxalic acid, malonic acid, succinic acid, glutaric acid, adipic acid, and the like, and alkene dicarboxylic acid such as maleic acid, fumaric acid, and the like; alicyclic dicarboxylic acid, for example, cycloalkane dicarboxylic acid such as cyclohexane dicarboxylic acid, and the like, and di- or tri-cycloalkane dicarboxylic acid, such as decalin dicarboxylic acid, norbornane dicarboxylic acid, adamantine dicarboxylic acid, and the like; aromatic dicarboxylic acid, for example, arene dicarboxylic acid such as terephthalic acid, isophthalic acid, phthalic acid, 2,6-naphthalene dicarboxylic acid, 1,8-naph- In Chemical Formula 8, R is as described above.

A schematic synthesis scheme for the copolymers represented by Chemical Formulas 7 and 8 is shown in FIG. 1.

The preparation method of the copolymer is not particularly limited, and a general copolymerization method known in the art may be applied.

Lens

A lens according to an embodiment of the present disclosure comprises a copolymer of a fluorene derivative represented by Chemical Formula 1, such as a polyester copolymer, and can be obtained by molding the copolymer or by other suitable methods including grinding, polishing, etc.

In some embodiments, the fluorene derivative and the copolymer thereof can be as described above, and a description thereof can be found above.

In some embodiments, the lens comprising the copolymer of the fluorene derivative can have high refractive characteristics, and the overall optical characteristics such as transparency, and the like, can be excellent.

In some embodiments, a lens according to an embodiment of the present invention may be obtained, for example, by injection molding the copolymer of the fluorene derivative in a lens shape using an injection molding machine or injection press molding machine.

In some embodiments, a lens may be used in an aspheric lens shape or other shape as desired or needed. The lens, such as an aspheric lens, can be used as an element in a camera lens among optical lenses. One or more coating layers, such as anti-reflection layer(s) and/or hard coating layer(s) and/or additional layer(s) as are used with optical devices may be formed alone or in combination on a surface of the lens as desired or needed.

In some embodiments, a lens may also be used in various applications such as in or as a part of a pickup lens, an f-θ lens, a glasses lens, and the like.

In some embodiments, a lens may be used as a lens or a portion of a lens of a single lens reflex camera, a digital still camera, a video camera, a mobile phone with a camera, a film having a lens therein, a telescope, a binocular telescope, a microscope, a projector, or the like.

Hereinafter, embodiments of the present disclosure will be described with reference to Examples, but the present disclosure is not limited thereto.

Example 1

Synthesis of Di-Substituted Benzyl Fluorene Ethanol Represented by Chemical Formula 4

After 400 ml of acetonitrile was put into a 3 L reactor equipped with a reflux apparatus as a reaction solvent, 9-fluorenon, 2-benzylphenol, and 3-mercaptopropionic acid were sequentially added thereto and dissolved therein at 25±2° C. A temperature was maintained at 80° C. for 1 hour while slowly dropping sulfuric acid, which was a reaction solvent, in the reactor, and a reaction end point was confirmed using thin layer chromatography (TLC). The reactor was cooled to and maintained at room temperature, and potassium carbonate aqueous solution was dropped to thereby neutralize a reaction solution, thereby obtain crystalline crude. The obtained crude was re-crystallized using hexane and methylene chloride, thereby obtaining di-substituted benzyl fluorene intermediate (HPLC purity: 99.2% (wt.), yield: 91%). 100 g of the obtained di-substituted benzyl fluorene was put into a 2 L three-neck reactor equipped with a reflux apparatus and dissolved using dimethyl sulfoxide, which was a reaction solvent. Then, ethylene carbonate and 2-methyl imidazole were sequentially added thereto under reflux at 145° C., and a reaction end point was confirmed using TLC. After the reaction was terminated, the reactor was cooled to 50° C., 500 ml of methanol was dropped therein to crystallize the reactant, and then, the reactor was cooled to room temperature. The obtained crude was dissolved in ethyl acetate and precipitated in distilled water, such that di-substituted benzyl fluorene ethanol represented by Chemical Formula 4 was obtained and dried under reduced pressure. HPLC purity: 99.2% (wt.), yield: 60%, $^1$H-NMR (CDCl$_3$, δ): 3.89 (benzyl, CH$_2$)

Figure 2:
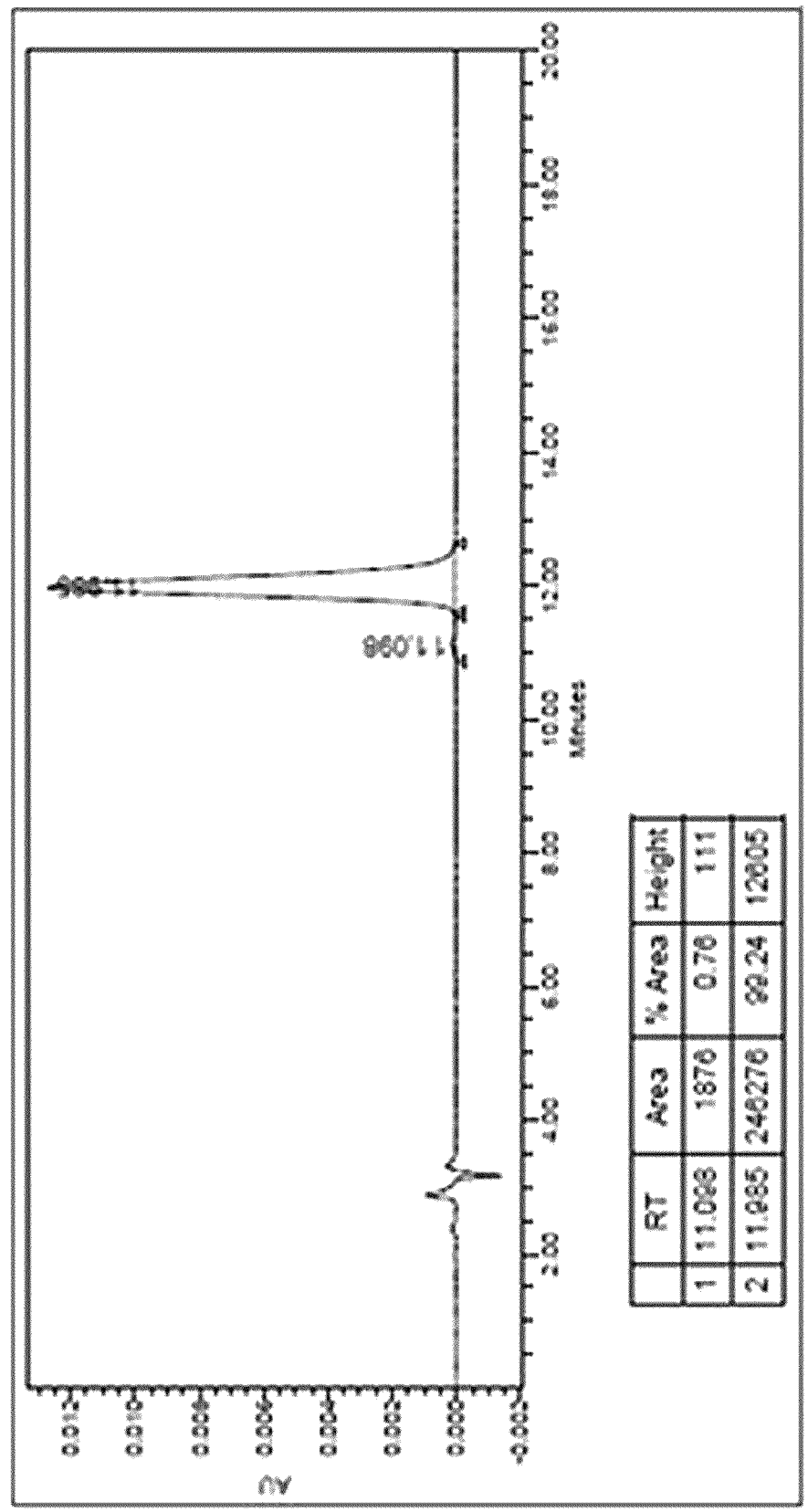
FIG. 2 is a high-performance liquid chromatography (HPLC) result of a compound obtained in Example 1.
Figure 3:
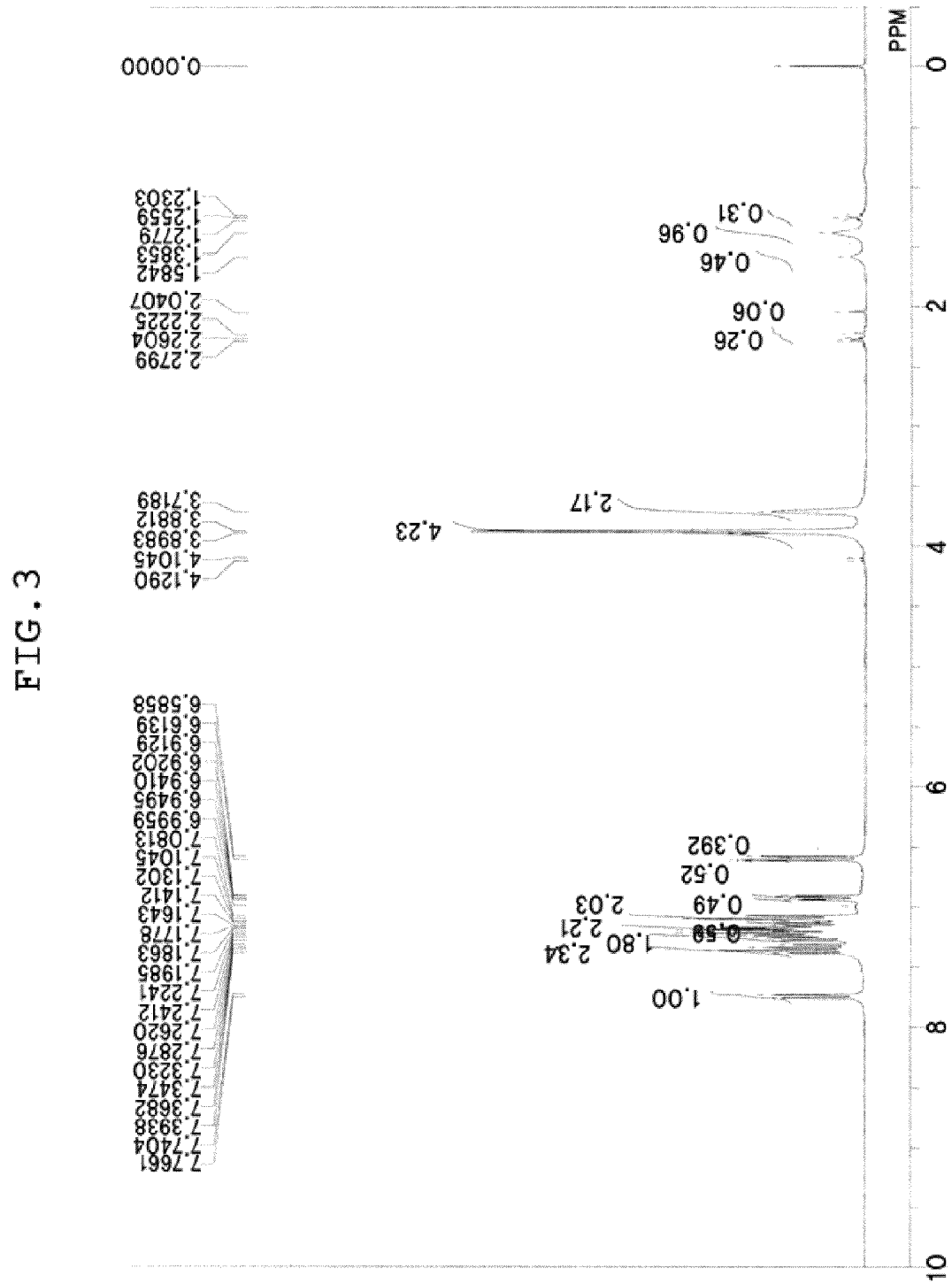
FIG. 3 is a hydrogen-nuclear magnetic resonance ($^1$H-NMR) result of the compound obtained in Example 1.

HPLC results and $^1$H-NMR results of the obtained compound were shown in FIGS. 2 and 3, respectively.

Example 2

Synthesis of Tetra-Substituted Benzyl Fluorene Ethanol Represented by Chemical Formula 3

[Reaction Formula 6]

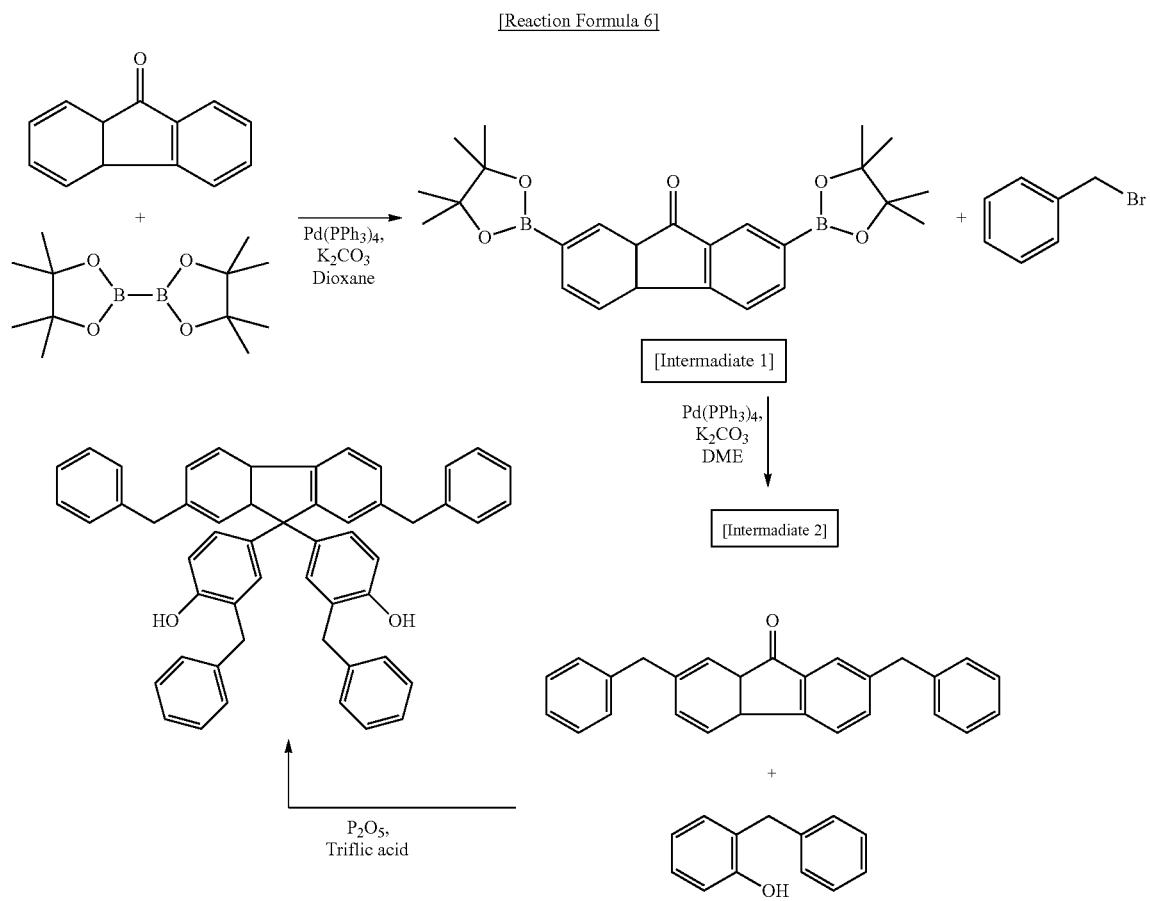

The reaction was carried out as described below with reference to Reaction Formula 6.

Intermediate 1

Synthesis of 2-(1,5-dimethyl-2,4-dioxa-3-borabicyclo[3.1.0]hexan-3-yl)-7-(4,4,5,5-tetramethyl-1,3,2-dioxaborolan-2-yl)-9H-fluoren-9-one)

After 2500 ml of 1,4-dioxane was put into a 12 L reactor equipped with a reflux apparatus as a reaction solvent, 500 g of 2,7-dibromo-9H-fluoren-9-one, 902 g of bis(pinacolato) diboron, 50 g of Pd(PPh$_3$)$_4$, and 613 g of potassium carbonate were injected into the reactor, respectively, and stirred/dissolved, followed by reflux at 100° C. for 30 hours or more. Then, a reaction end point was confirmed using TLC. The reactor was cooled to mom temperature, and a large excess of methylene chloride was put into the reactor to dissolve the crude. Next, activated carbon was added thereto and stirred, and then the resultant was filtered. After a large excess of distilled water was put into the filtered filtrate to remove by-products, a methylene chloride layer was separated and condensed. The obtained crude was re-crystallized using an ethyl acetate/hexane (1:12) mixed solvent, and the obtained crystal was filtered and dried, thereby obtaining intermediate 1 (synthesis yield: 68%).

Intermediate 2

Synthesis of 2,7-dibenzyl-9H-fluoren-9-one

After 1100 ml of dimethoxy ethane was put into a 12 L reactor equipped with a reflux apparatus as a reaction solvent, 270 g of intermediate 1, at least two equivalents of benzylbromide, 27 g of Pd(PPh$_3$)$_4$, and 260 g of potassium carbonate were injected into the reactor, respectively, and stirred/dissolved, followed by reflux at 80° C. for 30 hours or more. Then, a reaction end point was confirmed using TLC. The reactor was cooled to mom temperature, and a large excess of methylene chloride was put into the reactor to dissolve the crude. Next, activated carbon was added thereto and stirred, and then the resultant was filtered. After a large excess of distilled water was put into the filtered filtrate to remove by-products, a methylene chloride layer was separated and condensed. The obtained crude was re-crystallized using an ethyl acetate/hexane (1:12) mixed solvent, and the obtained crystal was filtered and dried, thereby obtaining intermediate 2 (synthesis yield: 73%).

[Tetra-Substituted Benzyl Fluorene]

164 g of intermediate 2 and 355 g of 2-benzyl phenol were put into a 2 L reactor equipped with a reflux apparatus, respectively, and then stirred. A temperature was maintained at 50° C. for 6 hour while slowly dropping P$_2$O$_5$, which is a reaction catalyst, and a suitable amount of trifluoromethanesulfonic acid in the reactor, and a reaction end point was confirmed using TLC. The reactor was cooled to and maintained at mom temperature, and the crude was extracted using 1000 ml of methylene chloride and distilled water. Thereafter, the obtained methylene chloride layer was additionally extracted with sodium bicarbonate aqueous solution two times, thereby separating and condensing the methylene chloride layer. The reaction solution was neutralized by dropping potassium carbonate aqueous solution, thereby obtaining crystalline crude. The obtained crude was re-crystallized with ethylacetate/hexane (1:4) mixed solution, and the obtained crystal was filtered and dried, thereby obtaining tetra-substituted benzyl fluorene, which was a final product. HPLC purity: 99.2% (wt.), yield: 52%, $^1$H-NMR (CDCl$_3$, δ): 3.86, 3.96 (benzyl, CH$_2$)

Figure 4:
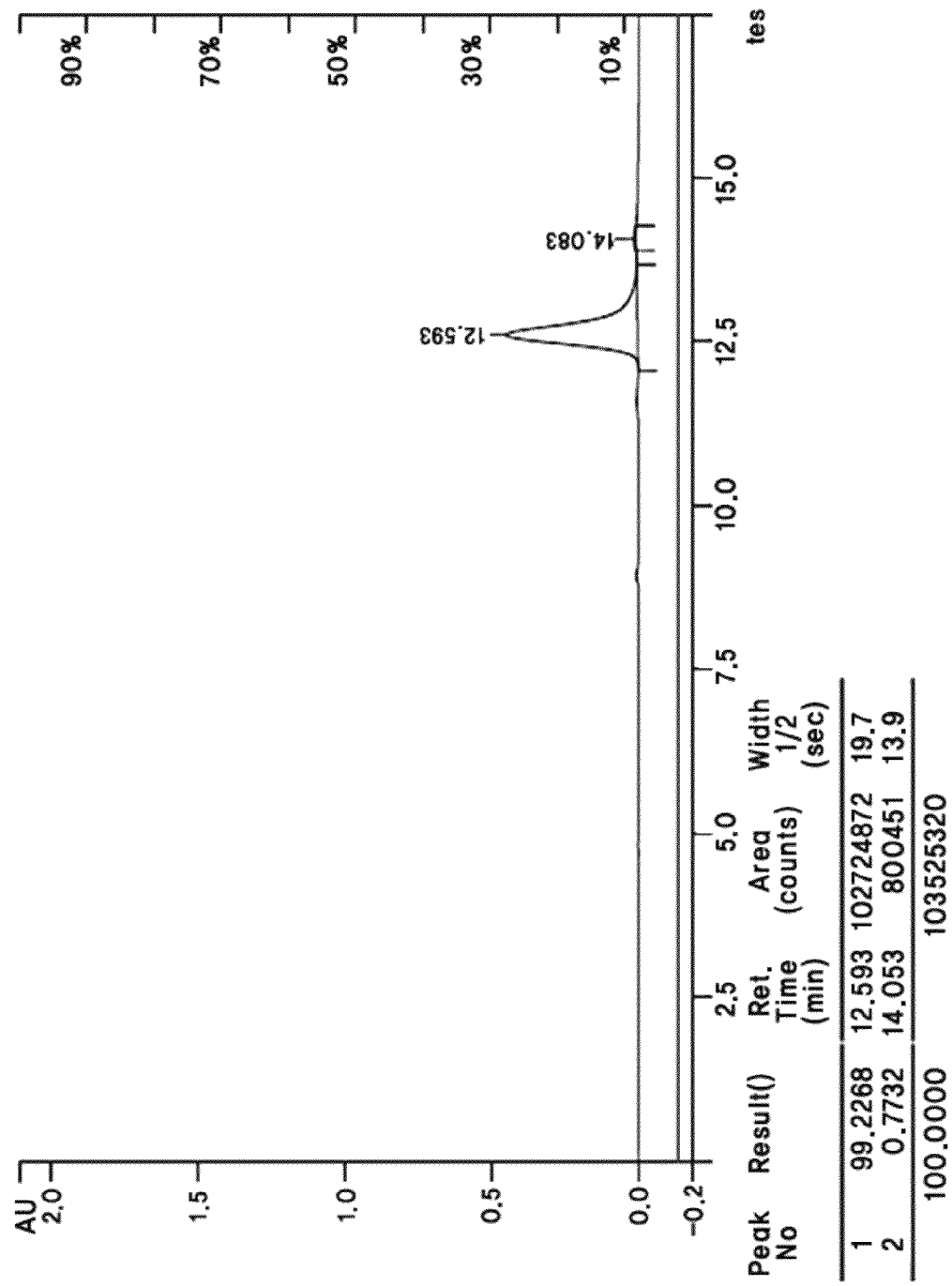
FIG. 4 is a HPLC result of a compound obtained in Example 2.
Figure 5:
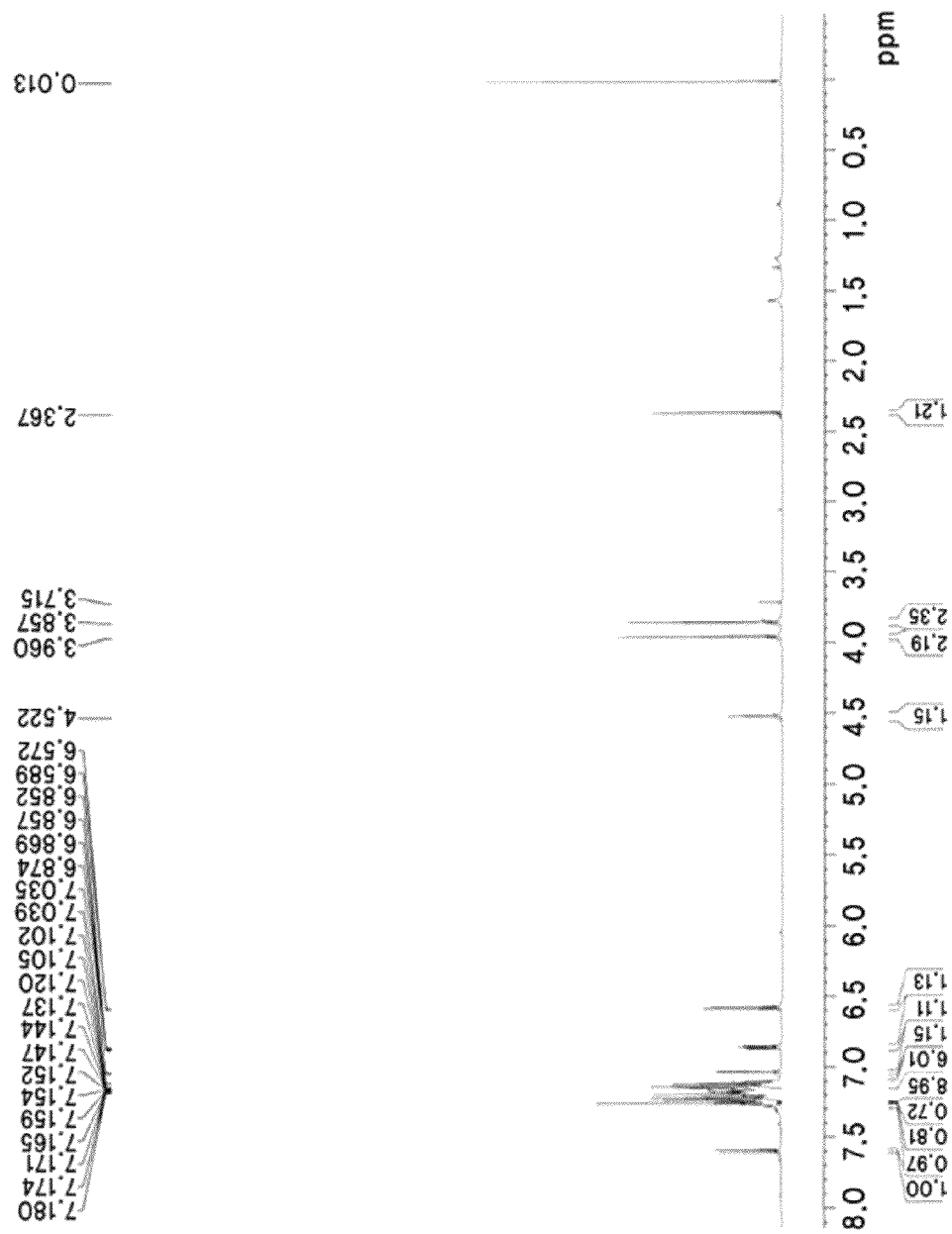
FIG. 5 is a $^1$H-NMR result of the compound obtained in Example 2.

HPLC results and $^1$H-NMR results of the obtained compound were shown in FIGS. 4 and 5, respectively.

[Tetra-Substituted Benzyl Fluorene Ethanol]

Ethanolysis of the obtained tetra-substituted benzyl fluorene was performed, thereby synthesizing the compound represented by Chemical Formula 3.

Example 3

Synthesis of Copolymer Based on Di-Substituted Benzyl Fluorene

A polymer was obtained by dissolving a di-substituted benzyl fluorene monomer having a purity of 99% (wt.) or more in a mixed solution of a sodium hydroxide aqueous solution and methylene chloride and performing a carbonation reaction using phosgene gas. Gel permeation chromatography (GPC) molecular weight and Tg of the polymer were shown in Table 1. Di-substituted benzyl fluorene ethanol was also prepared by the same synthetic method.

TABLE 1

| Sample | GPC Molecular Weight | | | DSC | TGA |
| --- | --- | --- | --- | --- | --- |
| | Mn, *1000 | Mw, *1000 | Mw/Mn | Tg (° C.) | Td 5 wt % (° C.) |
| Di-substituted Benzyl Fluorene | 15.8 | 63.1 | 4.0 | 131 | 477 |
| Di-substituted Benzyl Fluorene ethanol | 12.8 | 35.0 | 2.7 | 130 | 479 |

Example 4

Synthesis of Copolymer Based on Tetra-Substituted Benzyl Fluorene

A polymer was obtained by dissolving a tetra-substituted benzyl fluorene monomer having a purity of 99% (wt.) or more in a mixed solution of sodium hydroxide aqueous solution and methylene chloride and performing a carbonation reaction using phosgene gas. Gel permeation chromatography (GPC) molecular weight and Tg of the polymer were shown in Table 2. Tetra-substituted benzyl fluorene ethanol was also prepared by the same synthetic method.

TABLE 2

| Sample | GPC Molecular Weight | | | DSC | TGA |
| --- | --- | --- | --- | --- | --- |
| | Mn, *1000 | Mw, *1000 | Mw/Mn | Tg (° C.) | Td 5 wt % (° C.) |
| Tetra-substituted Benzyl Fluorene | 16.0 | 81.0 | 5.1 | 142 | 460 |
| Tetra-substituted Benzyl Fluorene Ethanol | 18.2 | 92.3 | 5.1 | 140 | 470 |

Example 5

Evaluation of Lens Characteristics

After each of the polymers obtained in Examples 3 and 4 and an existing high refractive resin (reference) was put into a mold having a width of 2 cm, a length of 2 cm, and a thickness of 1 mm and melted by heating, the mold was removed, thereby manufacturing a plate shaped sample for evaluating lens optical characteristics. Then, a refractive index, an abbe number, and transmittance of each of the samples were measured. The results were shown in Table 3.

TABLE 3

| Sample | Refrective Index 587 nm, 25° C. | ABBE number | Transmittance |
| --- | --- | --- | --- |
| Polymer Based on Di-substituted Benzyl Fluorene | 1.652 | 24 | 95% |
| Polymer Based on Tetra-substituted Benzyl Fluorene | 1.660 | 23 | 94% |
| Reference | 1.635 | 24 | 85% |

As shown in Table 3, the polymer for a lens according to the present invention had a high refractive index of about 1.660, high transmittance of 90% or more, and a low Tg suitable for injection molding.

As described above in the examples, in the fluorene derivative according to an embodiment of the present disclosure, an awl group having a low molecular volume is provided in at least two of the groups which are attached to two or more benzene moieties of Formula 1, and the polarity of the fluorene derivative itself can be increased, and the refractive index can be improved.

Further, an alkanediyl group of the R1-4 group, having a rotatable single bond is provided in the R5 group which is attached to the aromatic ring of Formula 1, such that Tg may be decreased. As a result, the viscosity may be decreased, and workability and formability may be improved.

In addition, in the fluorene derivative of the examples, a halogen substituent such as Br or Cl was not introduced to the fluorene structural unit, and a more eco-friendly product and process was obtained and a reduced or eliminated potential for dioxin side-products or contaminants resulted. Further, in the fluorene derivative of the examples, sulfur and nitrogen were not introduced to the fluorene structural unit, and the lens exhibited improved optical characteristics and improved transparency.

Although embodiments of the present disclosure have been disclosed for illustrative purposes, it will be appreciated that the present disclosure is not limited thereto, and those skilled in the art will appreciate that various modifications, additions and substitutions are possible, without departing from the scope and spirit of the invention.

Accordingly, any and all modifications, variations or equivalent arrangements should be considered to be within the scope of the invention, as defined in the claims and their equivalents.

REFERENCES

1. Japanese Patent Laid-Open Publication No. 2001-106761

What is claimed is:

1. A fluorene derivative represented by the following Chemical Formula 1:

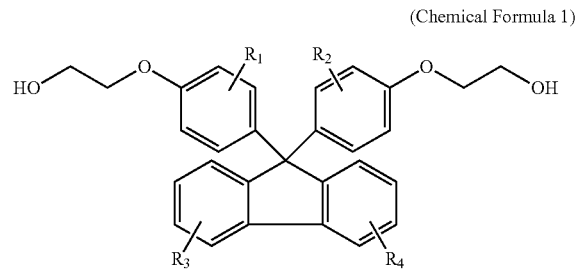

(Chemical Formula 1)

wherein $R_1$, $R_2$, $R_3$, and $R_4$ are the same as or different from each other and are H or represented by the following Chemical Formula 2, and at least two of $R_1$, $R_2$, $R_3$, and $R_4$ are independently selected from compounds represented by the following Chemical Formula 2:

—$R_5$—Ar       (Chemical Formula 2)

wherein $R_5$ is a (C1-C5) alkanediyl group, and Ar is a (C6-C22) aryl group.

2. The fluorene derivative of claim 1, wherein Ar is a phenyl group.

3. The fluorene derivative of claim 1, wherein Ar is a naphthyl group.

4. The fluorene derivative of claim 1, wherein Ar is a biphenyl group.

5. The fluorene derivative of claim 1, wherein Ar is an anthryl group.

6. The fluorene derivative of claim 1, wherein Ar is a phenanthryl group.

7. The fluorene derivative of claim 1, wherein the compound represented by Chemical Formula 1 is a compound represented by the following Chemical Formula 3

(Chemical Formula 3)

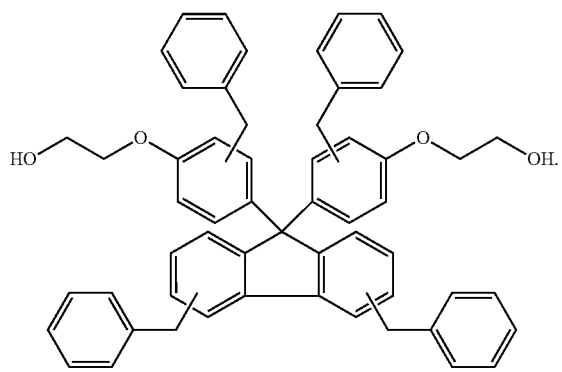

8. The fluorene derivative of claim 1, wherein the compound represented by Chemical Formula 1 is a compound represented by the following Chemical Formula 4

(Chemical Formula 4)

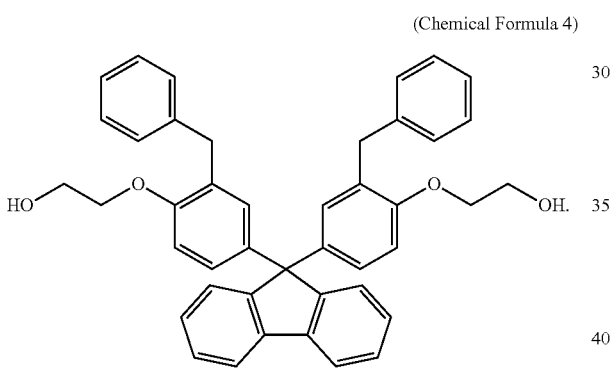

9. The fluorene derivative of claim 1, wherein the compound represented by Chemical Formula 1 is a compound represented by the following Chemical Formula 5

(Chemical Formula 5)

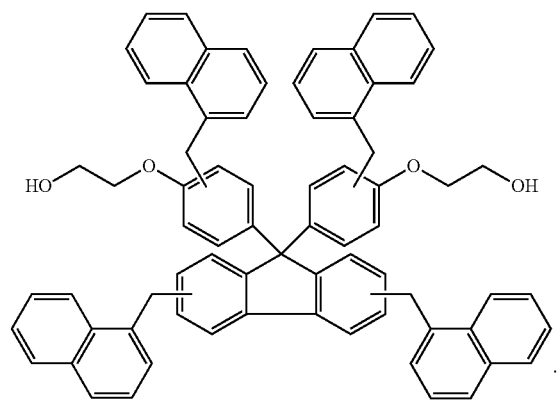

10. The fluorene derivative of claim 1, wherein the compound represented by Chemical Formula 1 is a compound represented by the following Chemical Formula 6

(Chemical Formula 6)

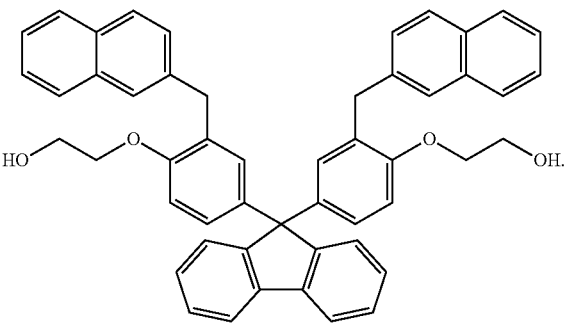

11. A copolymer of a compound represented by the following Chemical Formula 1:

(Chemical Formula 1)

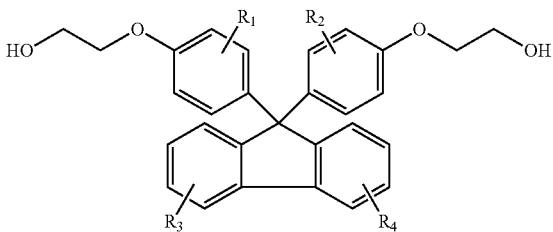

wherein $R_1$, $R_2$, $R_3$, and $R_4$ are the same as or different from each other and are H or represented by the following Chemical Formula 2, and at least two of $R_1$, $R_2$, $R_3$, and $R_4$ are independently selected from compounds represented by the following Chemical Formula 2:

—$R_5$—Ar  (Chemical Formula 2)

wherein $R_5$ is a (C1-C5) alkanediyl group, and Ar is a (C6-C22) aryl group.

12. A lens comprising a copolymer of a compound represented by the following Chemical Formula 1:

(Chemical Formula 1)

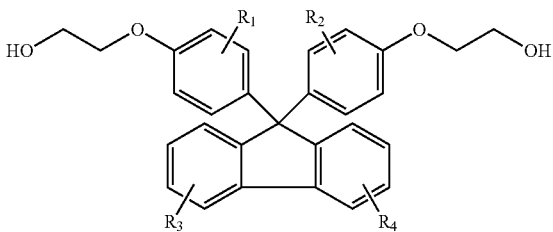

wherein $R_1$, $R_2$, $R_3$, and $R_4$ are the same as or different from each other and are H or represented by the following Chemical Formula 2, and at least two of $R_1$, $R_2$, $R_3$, and $R_4$ are independently selected from compounds represented by the following Chemical Formula 2:

—$R_5$—Ar  (Chemical Formula 2)

In Chemical Formula 2, $R_5$ is a (C1-C5) alkanediyl group, and Ar is a (C6-C22) aryl group.

13. A copolymer of a compound of Formula 3, Formula 4, Formula 5 or Formula 6 as shown below:

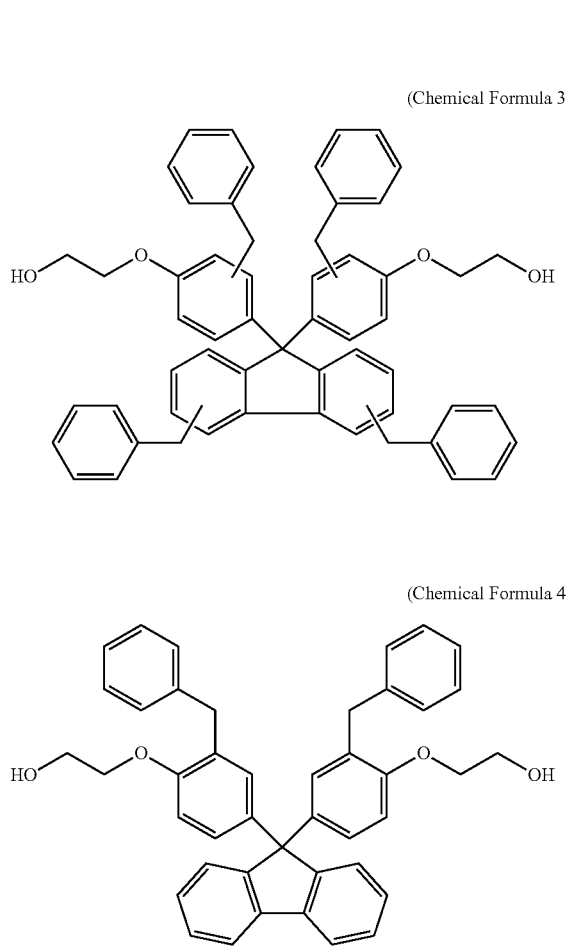

(Chemical Formula 3)

(Chemical Formula 4)

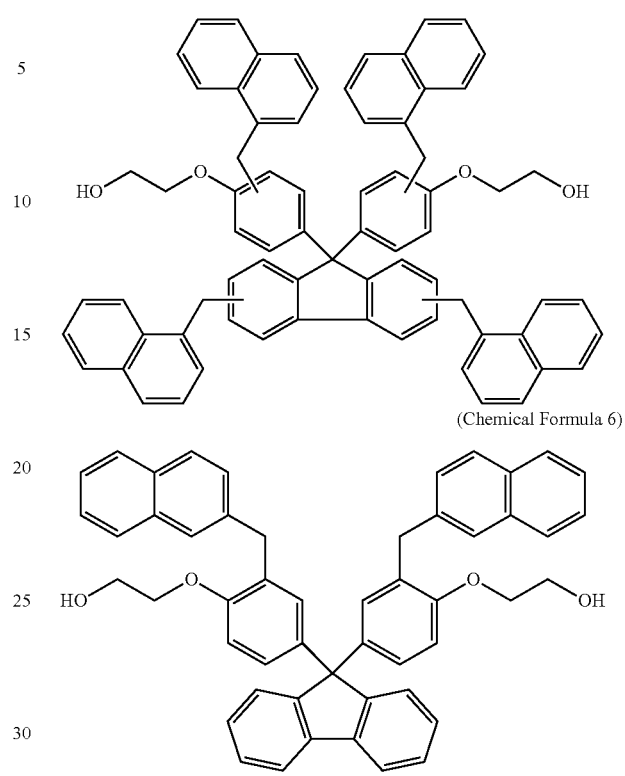

(Chemical Formula 5)

(Chemical Formula 6)

and of a dicarboxylic acid or phosgene.

14. A lens comprising the copolymer of claim 13.

15. The copolymer of claim 13, wherein the copolymer is a copolymer of two or more dicarboxylic acids.

16. The copolymer of claim 13, wherein the copolymer is a copolymer of phosgene.

* * * * *